(12) United States Patent
Aoki et al.

(10) Patent No.: US 12,288,602 B1
(45) Date of Patent: Apr. 29, 2025

(54) MEDICAL EXAMINATION SUPPORT SYSTEM, AND NON-TRANSITORY COMPUTER-READABLE MEDIUM THEREFOR

(71) Applicant: MOTOCLE Co., Ltd., Onojo (JP)

(72) Inventors: Motoki Aoki, Onojo (JP); Kokoro Umemoto, Onojo (JP)

(73) Assignee: MOTOCLE Co., Ltd., Onojo (JP)

( * ) Notice: Subject to any disclaimer, the term of this patent is extended or adjusted under 35 U.S.C. 154(b) by 0 days.

(21) Appl. No.: 18/999,619

(22) Filed: Dec. 23, 2024

(30) Foreign Application Priority Data

Feb. 1, 2024 (JP) .................................. 2024-014168

(51) Int. Cl.
| | | |
|---|---|---|
| G10L 15/26 | (2006.01) | |
| G06F 40/123 | (2020.01) | |
| G06F 40/30 | (2020.01) | |
| G16H 15/00 | (2018.01) | |

(52) U.S. Cl.
CPC .......... G16H 15/00 (2018.01); G06F 40/123 (2020.01); G06F 40/30 (2020.01); G10L 15/26 (2013.01)

(58) Field of Classification Search
None
See application file for complete search history.

(56) References Cited

U.S. PATENT DOCUMENTS

| | | | | |
|---|---|---|---|---|
| 9,953,640 | B2* | 4/2018 | Rice .......................... | G10L 15/08 |
| 11,830,612 | B2* | 11/2023 | Hoernig .................. | G16H 40/20 |
| 12,014,722 | B2* | 6/2024 | Sharma .................... | G10L 13/02 |
| 12,207,903 | B2* | 1/2025 | Shallom .................. | A61B 5/725 |
| 2005/0055215 | A1* | 3/2005 | Klotz ....................... | G10L 15/26 |
| | | | | 704/E15.045 |
| 2014/0249860 | A1* | 9/2014 | Rynchek ................. | G06Q 10/10 |
| | | | | 705/3 |
| 2017/0212603 | A1* | 7/2017 | Rahme ................... | G06F 3/0231 |
| 2023/0270484 | A1* | 8/2023 | Canady .................. | G06F 3/167 |
| | | | | 606/41 |
| 2023/0371889 | A1* | 11/2023 | Weston ................... | G10L 25/30 |
| 2023/0385021 | A1* | 11/2023 | Adams .................... | G06F 3/167 |
| 2024/0428002 | A1* | 12/2024 | Elangovan ............. | G06F 40/30 |

FOREIGN PATENT DOCUMENTS

| | | |
|---|---|---|
| JP | 2017-111190 A | 6/2017 |
| JP | 2018-206055 A | 12/2018 |
| JP | 2023-026640 A | 2/2023 |
| JP | 2023-048799 A | 4/2023 |
| JP | 7385320 B1 | 11/2023 |

* cited by examiner

*Primary Examiner* — Neeraj Sharma
(74) *Attorney, Agent, or Firm* — Muncy, Geissler, Olds & Lowe, P.C.

(57) ABSTRACT

In a medical examination support system 1, speech information of conversation between a veterinarian and a pet owner is converted into text data by a text data conversion unit 106. The text data and a template which is instruction content for a large language model 205 are input to a medical examination support information creation unit 204 as input parameters, and medical examination support information is automatically created from the text data on the basis of the large language model 205. The created medical examination support information is displayed on a monitor 3 by a display device 30.

8 Claims, 11 Drawing Sheets

Fig.4

| # | pronunciation | conversion1 | conversion2 |
|---|---|---|---|
| 1 | tjú:ner | tuner | tumor |
| 2 | sél | sell | cell |
| 3 | ... | ... | ... |
| 4 | ... | ... | ... |
| 5 | ... | ... | ... |
| ... | ... | ... | ... |

Fig.5A

| # | ID | TEMPLATE NAME | CATEGORY |
|---|---|---|---|
| 1 | xxxxxxxxx1 | GENERAL MEDICAL EXAMINATION | MEDICAL EXAMINATION CONVERSATION |
| 2 | xxxxxxxxx2 | DESCRIPTION OF SURGERY | MEDICAL EXAMINATION CONVERSATION |
| 3 | xxxxxxxxx3 | DESCRIPTION OF DISCHARGE | MEDICAL EXAMINATION CONVERSATION |
| 4 | xxxxxxxxx4 | FOLLOW-UP OBSERVATION + PRESCRIPTION DESCRIPTION | OWNER INSTRUCTIONS |
| 5 | xxxxxxxxx5 | PRESCRIPTION EXPLANATION ONLY | OWNER INSTRUCTIONS |
| ... | ... | ... | ... |

Fig.5B

| # | ID | MAIN TABLE ID | PROMPT |
|---|---|---|---|
| 1 | yyyyyyyy1 | xxxxxxxxx1 | <CHIEF COMPLAINT> PLEASE SUMMARIZE CONVERSATION FOCUSING ON "CHIEF COMPLAINT OF OWNER." PLEASE DESCRIBE PURPOSE OF TODAY'S EXAMINATION WITH OWNER'S EYES. |
| 2 | yyyyyyyy2 | xxxxxxxxx1 | <TEST INFORMATION/TREATMENT CONTENT> PLEASE DESCRIBE ORIENTATION OF TEST, TEST NAME, TEST RESULT, AND TREATMENT CONTENT. IF IT IS CONSIDERED IMPORTANT INFORMATION FROM CONFIRMATION OF INFORMATION RELATED TO EXAMINATION, PLEASE DESCRIBE IT IN DETAIL. |
| 3 | yyyyyyyy3 | xxxxxxxxx1 | <TREATMENT POLICY> IF YOU KNOW ABOUT PROPOSED TREATMENT POLICY AND TREATMENT PLAN, PLEASE WRITE BULLET POINTS FOR EACH POINT. |
| 4 | yyyyyyyy4 | xxxxxxxxx4 | GIVE INSTRUCTIONS FOR FOLLOW-UP EXAMINATION PROVIDED BY VETERINARIAN TO OWNER OF SMALL DOG DIAGNOSED WITH HEPATIC ENCEPHALOPATHY. GENERATE CONTENT INCLUDING SPECIFIC INSTRUCTIONS ON IMPORTANT OBSERVATION POINTS, HOW TO RECORD SYMPTOMS, AND WHAT TO DO IN CASE OF EMERGENCY. |
| 5 | yyyyyyyy5 | xxxxxxxxx5 | GIVE, TO OWNER, FOR CORRECT DOSAGES (LACTULOSE, METRONIDAZOLE, AND ZINC SUPPLEMENTS) PRESCRIBED BY VETERINARIAN FOR TREATMENT OF HEPATIC ENCEPHALOPATHY. PLEASE GENERATE CONTENT INCLUDING SPECIFIC INSTRUCTIONS FOR DOSAGES, ADMINISTRATION INTERVAL, AND HOW TO DEAL WITH SIDE EFFECTS. |
| ... | ... | ... | ... |

Fig.6

| # | ID | PRODUCT NAME | ADDITIONAL PRODUCTS | FEE |
|---|---|---|---|---|
| 1 | yyyyyy1 | BLOOD TEST / 17 ITEMS | ○ | xxxx |
| 2 | yyyyyy2 | BLOOD TEST/ 5 ITEMS | ○ | xxxx |
| 3 | yyyyyy3 | OUTSOURCED BLOOD TEST | ○ | xxxx |
| 4 | yyyyyy4 | URINE TEST/GENERAL | - | xxxx |
| 5 | yyyyyy5 | URINE TEST/ GENERAL + SEDIMENTATION | - | xxxx |
| 6 | yyyyyy6 | ABDOMINAL ECHO | - | xxxx |
| 7 | yyyyyy7 | ABDOMINAL X-RAY TEST/ 1 SHEET | - | xxxx |
| 8 | yyyyyy8 | FIVE-TYPE MIXED VACCINE FOR DOGS | - | xxxx |
| 9 | yyyyyy9 | SUBCUTANEOUS DRIP | ○ | xxxx |
| ... | ... | ... | ... | ... |

Fig.8

MEDICAL EXAMINATION SUPPORT INFORMATION

| VETERINARIAN IN CHARGE | OWNER NAME | PET NAME |

| MEDICAL EXAMINATION TEMPLATE | SPEECH INPUT TERMINAL |

MEDICAL RECORD | SUMMARY | MEDICAL EXAMINATION DETAILS

- MY PET SUDDENLY FELL DOWN AND STARTED TO CRAMP.
- I SEE. HOW LONG DID ATTACK LAST?
- IT SEEMS TO BE MORE THAN SEVERAL MINUTES.
- I UNDERSTAND. WAS PET CONSCIOUS DURING ATTACK?
- PET SEEMED SLIGHTLY CONSCIOUS.
- HAS PET HAD THIS KIND OF ATTACK SO FAR?
- NO, THIS IS MY FIRST TIME.
- I RECOMMEND BLOOD TESTS AND BRAIN IMAGING.
- I UNDERSTAND. WHAT KIND OF TREATMENT IS REQUIRED?
- ANTIEPILEPTIC MEDICINE IS USUALLY PRESCRIBED IN CASE OF EPILEPSY.
- I UNDERSTAND. DOES PET NEED ANY SPECIAL CARE?

CHIEF COMPLAINT:
- BODY ATTACK
- STATE OF CONFUSION AFTER ATTACK
- STATE OF CONFUSION

OWNER'S ANXIETY:
- ATTACK SITUATIONS
- CAUSES OF ATTACK
- INTERNAL THERAPY IS DESIRED

DIAGNOSIS:
- HEPATIC ENCEPHALOPATHY
- METABOLIC DISEASES
- INITIAL DIAGNOSIS

ORIENTATION OF TEST:
- BLOOD TEST
- BRAIN CT SCAN
- RECORDING AND OBSERVATION OF ATTACK

TREATMENT PLAN:
- IDENTIFICATION OF SHUNT BLOOD VESSELS
- PERIODIC BLOOD TESTS
- CONSIDER SURGICAL REMEDIATION

PRESCRIPTION:
- LACTULOSE
- METRONIDAZOLE
- LOW-PROTEIN DIET

NEXT VISIT TO HOSPITAL:
- TALK WITH YOUR FAMILY ABOUT TREATMENT AND TALK OVER PHONE ABOUT YOUR NEXT VISIT

OTHERS:
- RE-EXAMINATION SCHEDULE
- EXERCISE RESTRICTION AND STRESS MANAGEMENT

WHOLE SPEECH REPRODUCTION

Fig.9

MEDICAL EXAMINATION SUPPORT INFORMATION

[MEDICAL RECORD] [SUMMARY] [MEDICAL EXAMINATION DETAILS]

REQUEST TO OWNER
TARGET PET PATIENT NAME:XXX
        VETERINARIAN IN CHARGE:YYY
        yyyy/mm/dd THIS IS WHAT I EXPLAINED DURING EXAMINATION TODAY.
(1) STRICT ADHERENCE TO DRUG TREATMENT
 ・
 ・
(2) MEAL MANAGEMENT
 ・
 ・
(3) REGULAR HEALTH CHECK
 ・
 ・
(4) ATTACK MONITORING
 ・
 ・
(5) ENVIRONMENTAL MANAGEMENT
 ・
 ・

PROTECT YOUR PET FROM EXCESSIVE EXERCISE AND STIMULATING ENVIRONMENT

---

[VETERINARIAN IN CHARGE] [OWNER NAME] [PET NAME]
[MEDICAL EXAMINATION TEMPLATE] [SPEECH INPUT TERMINAL]

MY PET SUDDENLY FELL DOWN AND STARTED TO CRAMP!

I SEE. HOW LONG DID ATTACK LAST?

IT SEEMS TO BE MORE THAN SEVERAL MINUTES.

I UNDERSTAND. WAS PET CONSCIOUS DURING ATTACK?

PET SEEMED SLIGHTLY CONSCIOUS.

HAS PET HAD THIS KIND OF ATTACK SO FAR?

NO, THIS IS MY FIRST TIME.

I RECOMMEND BLOOD TESTS AND BRAIN IMAGING.

I UNDERSTAND. WHAT KIND OF TREATMENT IS REQUIRED?

ANTIEPILEPTIC MEDICINE IS USUALLY PRESCRIBED IN CASE OF EPILEPSY.

I UNDERSTAND. DOES PET NEED ANY SPECIAL CARE?

[WHOLE SPEECH REPRODUCTION]

MEDICAL EXAMINATION SUPPORT SYSTEM, AND NON-TRANSITORY COMPUTER-READABLE MEDIUM THEREFOR

TECHNICAL FIELD

The present invention relates to a medical examination support system, a display device, and a medical examination support program. Specifically, the present invention relates to a medical examination support system, a display device, and a medical examination support program capable of creating a medical record with high quality on the basis of information of conversation between a veterinarian and an owner in animal medical care and improving the efficiency of animal medical care.

DESCRIPTION OF THE RELATED ART

Pets, including dogs and cats, are irreplaceable for humans, provide pleasure to owners' daily life and sometimes even mental support. In recent years, the demand for high-quality animal medical care has been expanding due to growing interest in the health of pets of owners.

Meanwhile, since animal medical care is outside of the range of national health insurance systems, the treatment cost for pet's injuries and diseases tends to be higher than the medical costs of humans. In animal medical care, a diagnosis/treatment method the same as or similar to that of human medical care is used. However, since a pet cannot directly tell a veterinarian its condition or a treatment request, a positive test is required to identify a disease state. Furthermore, it is necessary for an owner to remember to appropriately perform continuous medication and follow-up in accordance with a treatment plan at home, and the degree of understanding of the owner with respect to treatment is likely to affect the quality of animal medical care.

Therefore, in the field of animal medical care, so-called informed consent is important, in which a veterinarian gives a sufficient explanation of proposals and confirmation items regarding treatment and tests, a treatment cost, and the like to an owner, and the owner agrees with a treatment method and the like after sufficiently understanding the explanation, and such consensus building is regarded as important in improving the quality of animal medical care.

For consensus building between a veterinarian and an owner, a method of creating a medical record including a medical chart in which information regarding treatment of a pet is collected and recording medical examination content is generally used. In particular, in recent years, in order to improve the efficiency of medical work and the accuracy of medical examination through information sharing, the introduction of electronic medical charts has been promoted in the field of animal medical care as well as human medical care.

On the other hand, in the field of animal medical care, it is usually necessary for a nurse to keep an animal that is a target patient on an examination table at the time of medical examination, and during that time, a veterinarian needs to perform an interview with an owner and explanation of a treatment policy. Therefore, it is difficult to create a medical record simultaneously with examination due to personnel and physical restrictions. In particular, when there is a next owner waiting for medical examination, there is a demand for business efforts to shorten the waiting time of the owner as a customer, and temporal pressure is also applied, making it more difficult to create a medical record with a constant quality.

In order to solve such a problem, for example, Patent Document 1 discloses a conversation recording system that stores speech information of conversation between a medical worker and a patient, converts the speech information into text data for each speaker, arranges the converted text data in a dialogue form by the speaker, and stores the text data as sentence data. As a result, a medical worker can focus on an interview with a patient and an explanation of a treatment policy, and create a patient medical chart while checking sentence data after the explanation to the patient, so that it is possible to create a medical record with high quality.

PRIOR ART DOCUMENT

Patent Document

[Patent Document 1] Japanese Unexamined Patent Application Publication No. 2018-206055

SUMMARY OF THE INVENTION

Problem to be Solved by the Invention

However, since the conversation recording system disclosed in Patent Document 1 described above merely stores speech information of a speaker as text data, a medical record needs to be created by a veterinarian himself/herself. Therefore, even in the conversation recording system in Patent Document 1, there is a problem that a medical worker including a veterinarian is still busy with the creation of documents including medical records, and cannot escape from long working hours.

In addition, a veterinarian creates a medical record by his/her own judgment within a limited time, there has been little progress in standardization of entry content in the industry, and information sharing at the time of team medical care due to entry omission or input error is insufficient, which can cause medical accidents.

Furthermore, the explanation from a veterinarian is not necessarily content that can be easily understood by an owner, and in order to prevent problems with the owner for a treatment policy and a treatment cost in advance, creation of a summary for the owner in which a medical record is summarized in a more easily understandable manner is required as one of the medical examination services.

The present invention has been made in view of the above points, and an object of the present invention is to provide a medical examination support system, a display device, and a medical examination support program capable of creating a medical record with high quality on the basis of information of conversation between a veterinarian and an animal owner in animal medical care and improving the efficiency of animal medical care.

Means for Solving the Problem

In order to achieve the above object, a medical examination support system of the present invention includes: a speech information storage unit that stores speech information of conversation exchanged between a medical worker and a target person having a subject that is a medical examination target; a text data conversion unit that converts the speech information into text data; a template storage unit that stores a predetermined template including instruction content for a large language model for creating medical examination support information including at least one of a medical record for the medical worker, a summary for the target person corresponding to the medical record, and medical examination details based on medical examination content; and a medical examination support information creation unit that creates the medical examination support information on the basis of the large language model with the text data and the template as input parameters.

Here, by providing the speech information storage unit that stores speech information of conversation exchanged between a medical worker and a target person having a subject that is a medical examination target, the stored speech information can be used as data for subsequent calculation processing. Furthermore, by storing the speech information as an evidence record, it is possible to avoid problems with the target person for a treatment policy and a treatment cost.

Furthermore, by providing the text data conversion unit that converts the speech information into text data, speech information can be converted into text data.

In addition, by providing the template storage unit that stores predetermined template including instruction content for a large language model for creating medical examination support information including at least one of a medical record for the medical worker, a summary for the target person corresponding to the medical record, and medical examination details based on medical examination content, it is possible to prevent instruction content for the large language model from being different depending on a user (here, a medical worker) and to keep the quality of output of the large language model constant.

In addition, by providing the medical examination support information creation unit that creates the medical examination support information on the basis of the large language model with the text data and the template as input parameters, it is possible to automatically create input information to each input item of the medical examination support information from conversation content during medical examination. Therefore, since a user does not need create the medical examination support information by himself/herself, the user can concentrate on examination and treatment for a subject, and the efficiency of the medical examination operation can be improved.

In addition, in a case where at least one or more input items of a chief complaint, diagnosis content, a treatment plan, treatment content, a prescription, and an explanation of a test result are included as input items of the medical record of the medical examination support information, and the medical examination support information creation unit crates input information to each input item of the medical record on the basis of the large language model, it is possible to automatically create a medical record on the basis of the large language model according to the input items of the medical record prepared in advance.

In addition, in a case where at least one or more input items of a method of administering a prescription drug to the subject, meal management of the subject, monitoring of a condition of the subject, management of a living environment of the subject, and a next scheduled medical examination date of the subject are included as input items of the summary of the medical examination support information, and the medical examination support information creation unit creates input information to each input item of the summary on the basis of the large language model, it is possible to automatically create a summary on the basis of the large language model according to the input items of the summary for the target person prepared in advance.

In addition, in a case where the medical examination support system includes a fee storage unit that is associated with a medical fee corresponding to a medical examination item, and the medical examination support information creation unit calls a medical fee corresponding to a medical examination item extracted on the basis of the large language model from the fee storage unit and creates input information to an input item the medical examination details, it is possible to automatically create medical examination details according to the medical examination items extracted by the large language models from text data.

Furthermore, in a case where the text data conversion unit includes a phrase extraction unit that extracts a word/phrase specified on the basis of a predetermined criterion from text data obtained from the speech information, a word/phrase determination unit that determines whether or not the word/phrase is correct from the context of one sentence including the word/phrase extracted by the word/phrase extraction unit, and a word/phrase conversion unit that converts the word/phrase into a correct word/phrase on the basis of the context of one sentence including the word/phrase in a case where the word/phrase determination unit determines that the word/phrase is incorrect, it is possible to prevent erroneous conversion at the time of converting speech information into text data, and thus it is possible to create medical examination support information with higher quality.

In addition, in a case where the medical examination support system includes a medical examination support information storage unit that stores the medical examination support information created by the medical examination support information creation unit, and at the time of the next medical examination of the subject, basic information of the subject is acquired from the medical examination support information stored in the medical examination support information storage unit, basic information including any information such as a weight and a body temperature of the subject and past medical examination content and prescription content can be reflected in the medical examination support information created in the current medical examination. Therefore, it is not necessary to input the basic information of the subject at the time of creating the current medical examination support information, and it is possible to create the medical examination support information reflecting the previous medical examination content, so that it is possible to reduce a calculation load at the time of creating the medical examination support information and create the medical examination support information with higher quality.

In addition, in a case where the speech information stored in the speech information storage unit is subjected to a predetermined anti-tampering process, it is possible to enhance the evidence capability of the speech information.

In order to achieve the above object, a display device according to the present invention includes: a first display unit that creates text data in a time-series interactive format for each speaker on the basis of speech information of conversation exchanged between a medical worker and a target person having a subject that is a medical examination target, and displays the text data; a second display unit that displays at least one of medical examination support information obtained from the text data on the basis of a large language model, the medical examination support information including a medical record for the medical worker, a summary for the target person corresponding to the medical record, and medical examination details based on medical examination content, the second display unit being displayed in parallel with the first display unit; a selection unit that selects one piece of medical examination support information to be displayed on the second display unit among the pieces of medical examination support information; and a display control unit that causes the one piece of medical examination support information selected by the selection unit to be displayed on the second display unit.

Here, by providing the first display unit that creates text data in a time-series interactive format for each speaker on the basis of speech information of conversation exchanged between a medical worker and a target person having a subject that is a medical examination target and displays the text data, conversation content between the medical worker and the subject is displayed in a time-series manner. Therefore, it is possible to specify a speaker and confirm the conversation content backward. Furthermore, any conversation part can be easily specified through keyword search of text data.

In addition, by providing the second display unit that displays at least one of the medical examination support information obtained from the text data on the basis of the large language model and including the medical record for the medical worker, the summary for the target person corresponding to the medical record, and the medical examination details based on the medical examination content, a user can check the content of the medical examination support information created by the large language model.

In addition, by providing the selection unit that selects one piece of medical examination support information to be displayed on the second display unit among the pieces of medical examination support information, and the display control unit that causes the one piece of medical examination support information selected by the selection unit to be displayed on the second display unit, it is possible to display any medical examination support information selected by a user on the second display unit.

Furthermore, in a case where the medical record displayed on the second display unit includes at least one or more items of a chief complaint, diagnosis content, a treatment plan, treatment content, a prescription, and an explanation of a test result, which are created on the basis of the large language model, a user can check the medical examination content on the basis of the content of the medical record displayed on the second display unit.

In addition, in a case where the summary displayed on the second display unit includes at least one or more items of a method of administering a prescription drug to the subject, meal management of the subject, monitoring of a condition of the subject, management of a living environment of the subject, and a next scheduled medical examination date of the subject, which are created on the basis of the large language model, a user can explain the medical examination content to a target person in detail and in an easy-to-understand manner on the basis of the summary displayed on the second display unit.

Furthermore, in a case where the medical examination details displayed on the second display unit include a medical fee corresponding to a medical examination item extracted on the basis of the large language model, a user can explain the basis of the medical examination details such as a treatment cost to a target person in detail and in an easy-to-understand manner on the basis of the medical examination details displayed on the second display unit.

In order to achieve the above object, according to the present invention, there is provided a medical examination support program includes: a step of acquiring speech information of conversation exchanged between a medical worker and a target person having a subject that is a medical examination target; a step of converting the speech information into text data; a step of selecting a template including instruction content for a large language model for creating medical examination support information including at least one of a medical record for the medical worker, a summary for the target person corresponding to the medical record, and medical examination details based on medical examination content; a step of inputting the text data and the template to the large language model as input parameters; and a step of creating the medical examination support information from the text data on the basis of the large language model to which the input parameters have been input.

Here, by providing the step of acquiring speech information of conversation exchanged between a medical worker and a target person having a subject that is a medical examination target, the acquired speech information can be used as data for subsequent calculation processing. Furthermore, by storing the speech n as an evidence record, it is possible to avoid problems with the target person for a treatment policy and a treatment cost.

Further, by providing the step of converting speech information into text data, speech information can be converted into text data.

In addition, by providing the step of selecting a template including instruction content for a large language model for creating medical examination support information including at least one of a medical record for the medical worker, a summary for the target person corresponding to the medical record, and medical examination details based on medical examination content, it is possible to prevent instruction content for the large language model from being different depending on a user and to keep the quality of output of the large language model constant.

In addition, by providing the step of creating the medical examination support information from the text data on the basis of the large language model to which the input parameters have been input, medical examination support information is automatically created from a conversation record during the medical examination. Therefore, a user does not need to create the medical examination support information by himself/herself. Thus, the user can concentrate on examination and treatment for a subject, and the efficiency of the medical examination operation can be improved.

Advantageous Effects of the Invention

According to the medical examination support system, the display device, and the medical examination support program of the present invention, it is possible to create a medical record with high quality on the basis of information of conversation between a veterinarian and an owner in animal medical care and to improve the efficiency of animal medical care.

BRIEF DESCRIPTION OF THE DRAWINGS

FIG. 4 is a diagram illustrating an example of an erroneous conversion list stored in a dictionary storage unit.

FIGS. 5A and 5B are diagrams illustrating an example of data content stored in a template storage unit.

FIG. 6 is a diagram illustrating an example of data content stored in a fee storage unit.

FIG. 8 is a diagram illustrating an example of a display screen in a state in which a medical record of medical examination support information is displayed on a monitor.

FIG. 9 is a diagram illustrating an example of a display screen in a state in which a summary of the medical examination support information is displayed on the monitor.

MODES FOR CARRYING OUT THE INVENTION

Hereinafter, embodiments of the present invention relating to a medical examination support system, a display device, and a medical examination support program will be described with reference to the drawings, and are provided for understanding of the present invention.

Figure 1:
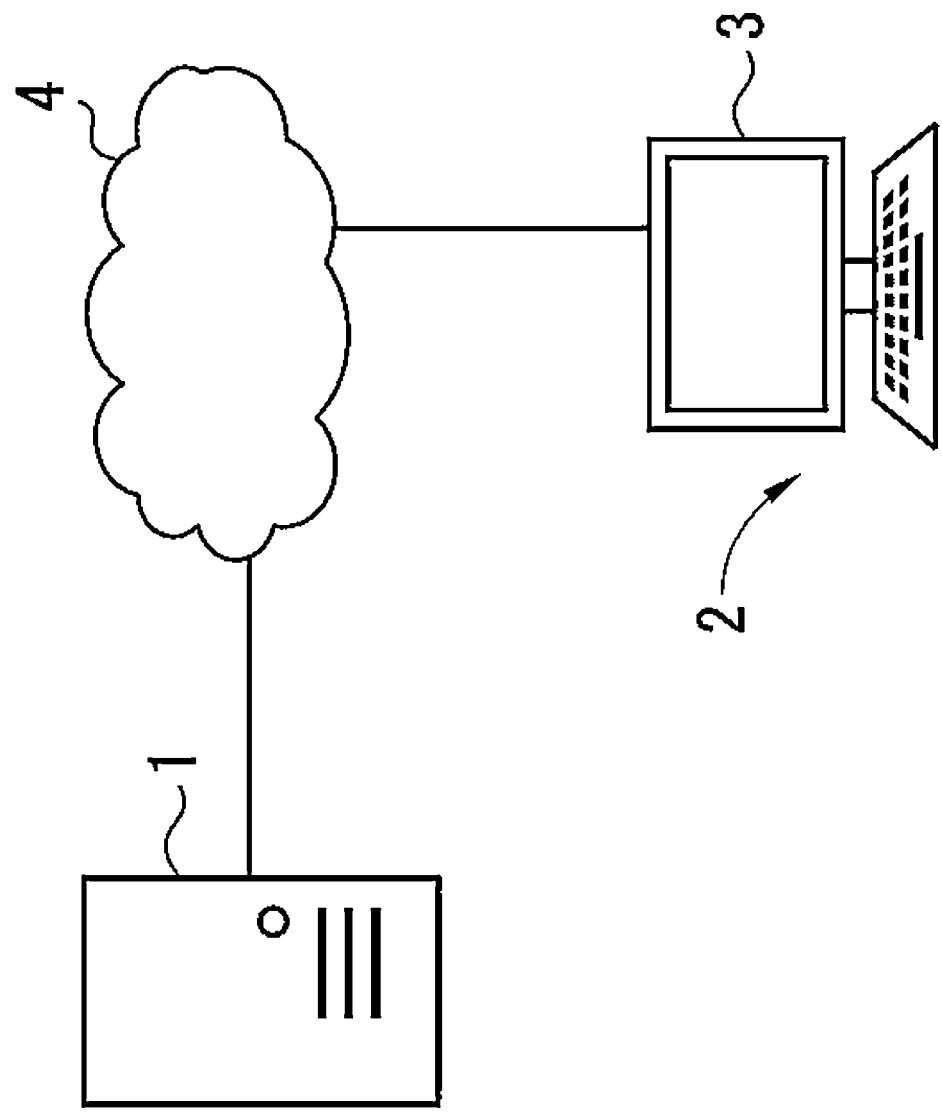
FIG. 1 is a diagram illustrating a state in which a medical examination support system and a terminal device according to an embodiment of the present invention are connected via an Internet line.

First, an outline of an entire network configuration including a medical examination support system 1 according to an embodiment of the present invention will be described with reference to FIG. 1. The medical examination support system 1 according to the embodiment of the present invention is a computer for operating a medical examination support program, and may be, for example, a server installed in a facility that provides medical examination services (in the embodiment of the present invention, a server installed in a veterinary hospital (hereinafter, referred to as a "hospital") that provides medical examination services for a subject that is a medical examination target (hereinafter, referred to as a "pet"), or a rental server (cloud server) in which the medical examination support program is installed.

A terminal device 2 is a personal computer used by a medical worker (a "veterinarian" in the embodiment of the present invention) at the time of medical examination, and the terminal device 2 and the medical examination support system 1 are communicatively connected to each other via an Internet line 4. Note that, in a case where the medical examination support system 1 is a cloud server or an on-premises server, a plurality of terminal devices 2 can simultaneously access the medical examination support system 1 via the Internet line 4 with respect to the medical examination support system 1.

Here, the medical examination support system 1 and the terminal device 2 are not necessarily connected to each other via the Internet line 4, and may be connected via any communication means. In addition, the terminal device 2 is not particularly limited as long as it is an information terminal having a communication function, such as a mobile terminal or a tablet terminal, in addition to a personal computer.

Figure 2:
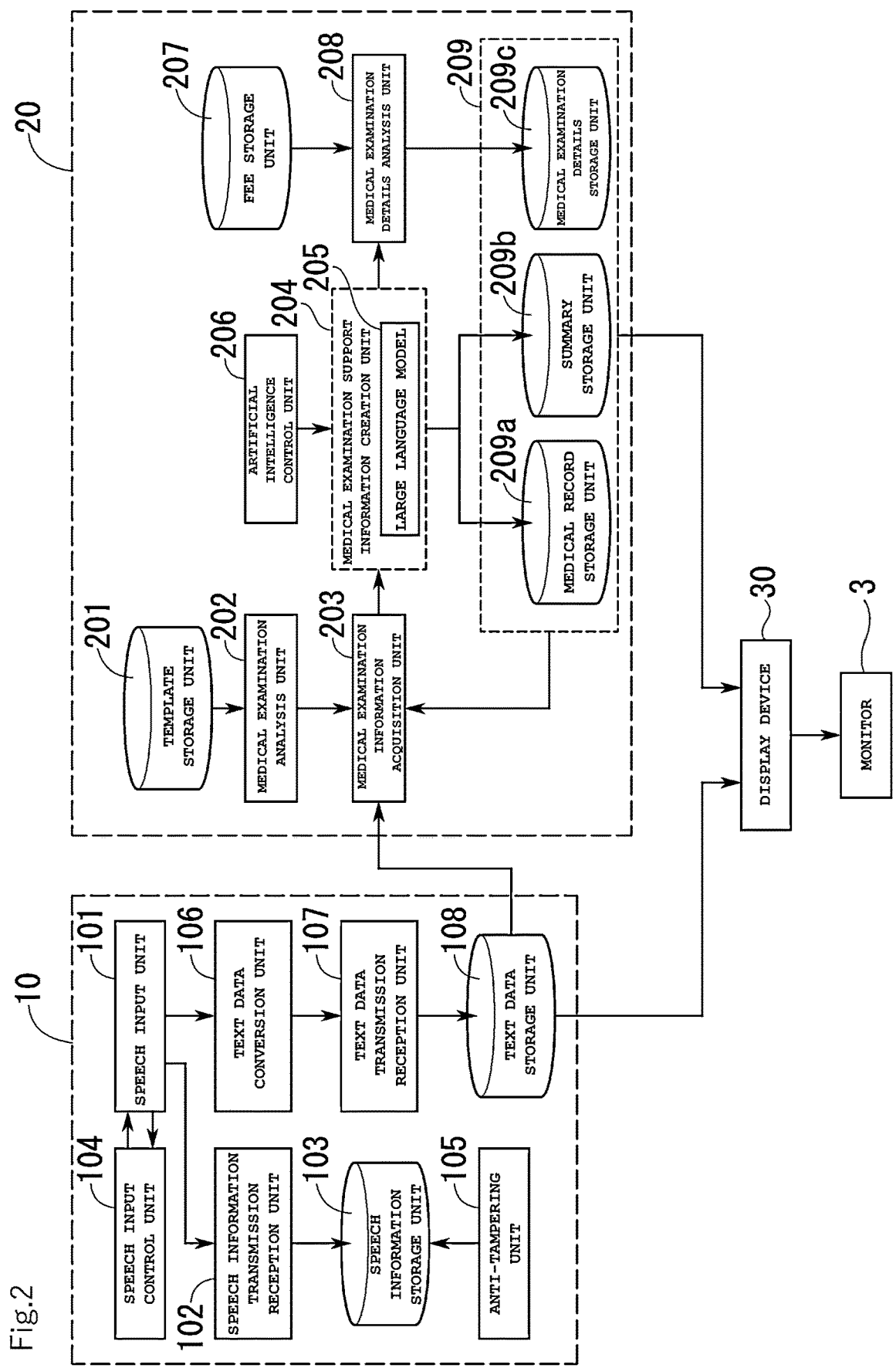
FIG. 2 is a block diagram illustrating an internal configuration of the medical examination support system.

Hereinafter, each configuration of the medical examination support system 1 will be described in detail with reference to FIG. 2. The medical examination support system 1 mainly includes a speech information system unit 10 that records conversation content exchanged between a veterinarian and a target person (a pet owner in the embodiment of the present invention) as speech information and performs a process of converting the speech information into text data, a medical examination support information system unit 20 that creates medical examination support information including a medical record on the basis of the text data processed by the speech information system unit 10, and a display device 30 that displays the text data of the conversation content and the medical examination support information on a monitor 3 of the terminal device 2.

1. Speech Information System Unit

First, a main configuration of the speech information system unit 10 will be described below.

[Speech Input Unit]

A speech input unit 101 has a function of collecting conversation during medical examination between a veterinarian and an owner with a microphone (not illustrated), and receiving input of the collected speech to acquire speech information. The speech information acquired by the speech input unit 101 is stored in a speech information storage unit 103 via a speech information transmission/reception unit 102.

[Speech Input Control Unit]

A speech input control unit 104 has a function of performing predetermined control by analyzing speech information input to the speech input unit 101 while controlling start and pause of speech input to the speech input unit 101.

For example, when detecting that a veterinarian utters the term "start," the speech input control unit 104 instructs the speech input unit 101 to start acquisition of speech information. In addition, when detecting that the veterinarian utters the term "stop," the speech input control unit 104 instructs the speech input unit 101 to stop acquisition of the speech information. As described above, it is possible to control start and stop of acquisition of speech information on the basis of a speech instruction from a veterinarian without operating the terminal device 2.

Here, terms used to execute the control of start and stop of the acquisition of the speech information are not limited to "start" or "stop," and a specific term may be registered in advance, and the control of the start or stop of the acquisition of the speech information may be performed on the basis of the registered language.

Furthermore, by operating a "start" button or a "stop" button displayed on the monitor 3 of the terminal device 2, it is also possible to control start and stop of acquisition of the speech information. However, by issuing an instruction to the speech input unit 101 on the basis of a speech instruction from a veterinarian, it is not necessary to stop examination by stopping the hand for operating the device, and it is possible to improve the efficiency of the medical examination operation.

In addition, the speech input control unit 104 analyzes the speech information received by the speech input unit 101, specifies a language used in the conversation and the number of speakers at the center of the conversation, and in a case where a volume of the speech information is small or in a case where it is determined that the speech information is interrupted due to deterioration in the communication environment, generates an error code, so that it is possible to notify the veterinarian that the speech information is incomplete and the speech input is not correctly performed.

Notification means here is not particularly limited, but for example, an error may be displayed as a warning screen on the monitor 3 of the terminal device 2 or a warning sound may be issued.

Furthermore, in a case where the speech input control unit 104 detects a silent time during which speech input to the speech input unit 101 is not detected for a certain period of time (for example, 2 to 3 seconds), the speech input control unit 104 recognizes conversation before and after the silent time as one phrase. Note that the phrase may be detected on the basis of real-time speech information input to the speech input unit 101, or the phrase may be detected after speech information of the entire conversation from the start to the end of the conversation is acquired.

[Anti-Tampering Unit]

An anti-tampering unit 105 has a function of performing an anti-tampering process for preventing tampering of the speech information stored in the speech information storage unit 103. As the anti-tampering process, for example, when the speech information is stored in the speech information storage unit 103, first, a hash code is generated from the content thereof by using a cryptographic hash function. Next, the hash code is digitally signed by using a secret key of a creator, and is added with a time stamp. As a result, tampering of a speech file can be effectively detected. The hash code is generated by using a cryptographic hash function, and a hash function used in the embodiment of the present invention is SHA-256.

Note that, in the embodiment of the present invention, SHA-256 is adopted as a hash function on the basis of strong security characteristics and adoption results in a wide range of fields, but the present invention is not necessarily limited thereto, and a hash function may be freely selected from generally used hash functions. For example, a hash function conforming to SHA-3 or other industry standards is also applicable.

Here, the speech information stored in the speech information storage unit 103 does not necessarily need to be subjected to the anti-tampering process. However, since it is possible to enhance the evidence capability of the speech information by performing the anti-tampering process, for example, when a problem for a treatment policy or a money trouble occurs between the veterinarian and the owner, it is possible to solve such trouble/problem in advance by using the speech information as circumstantial evidence.

[Text Data Conversion Unit]

A text data conversion unit 106 has a function of converting the speech information input from the speech input unit 101 into text data after transcription using artificial intelligence using a trained machine learning model.

Figure 3:
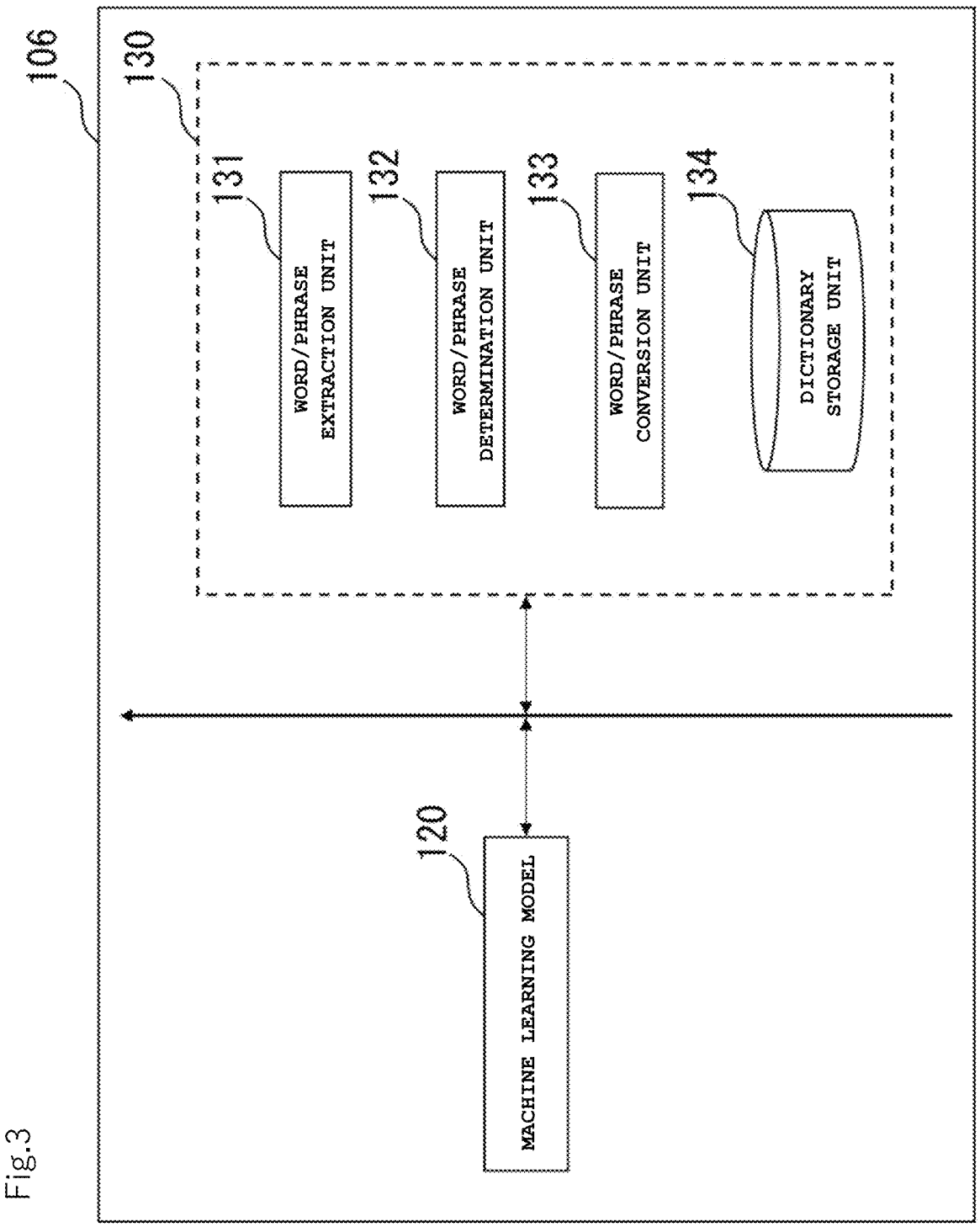
FIG. 3 is a block diagram illustrating an internal configuration of a text data conversion unit.

FIG. 3 illustrates a block diagram of an internal configuration of the text data conversion unit 106. As illustrated in FIG. 3, the text data conversion unit 106 includes a machine learning model 120 and an erroneous conversion prevention unit 130 that prevents erroneous conversion including homonyms at the time of transcription. The processing result by the erroneous conversion prevention unit 130 is fed back to the machine learning model 120 to perform additional learning, and the algorithm of the machine learning model 120 is optimized.

The erroneous conversion prevention unit 130 mainly includes a word/phrase extraction unit 131, a word/phrase determination unit 132, and a word/phrase conversion unit 133, and further includes a dictionary storage unit 134 in which a list of erroneous conversion (see FIG. 4) that is highly likely to occur with a technical term in the medical field is stored in advance.

For example, when it is detected that the speech information includes a pronunciation "tjúːner" registered as the erroneous conversion list, words the pronunciation "tjúːner" is extracted by the word/phase extraction unit 131. The word/phrase determination unit 132 determines which word of "tuner" in conversion 1 or "tumor" in conversion 2 is to be converted from "tjúːner" from the context before and after of a sentence including the pronunciation "tjúːner" As a result of the determination, when it is determined that the "tumor" in conversion 2 is correct, the speech information of "tjúːner" is converted into text data of "tumor" by the word/phrase conversion unit 133.

In addition, in the dictionary storage unit 134, not only the erroneous conversion list including homonyms, but also difficult drug names and medical terms, or words and phrases that are difficult to listen to and distinguish are registered in advance, so that it is possible to prevent erroneous conversion of words and phrases that are difficult to distinguish from speech information.

For example, there may be a case where a veterinarian pronounces "doxycycline" as a medicine name, but "d" in the beginning of the word is recognized as "t" as speech information, and the word is erroneously converted into text data as "toxycycline." Even in this case, when the word/phrase extraction unit 131 extracts the word "toxycycline" and then the word/phrase determination unit 132 determines that the veterinarian is explaining a medicine from the preceding and subsequent contexts, the word/phrase extraction unit determines that "toxycycline" should be converted into "doxycycline," and the word/phrase conversion unit 133 converts the word into text data.

Note that, in a case where it is necessary to add a homonym or a technical term that is not in the erroneous conversion list, a word or a phrase is added by an administrator of the medical examination support system 1 (a veterinarian in the embodiment of the present invention), and the machine learning model 120 is caused to learn the word or the phrase each time, so that it is possible to improve the conversion accuracy of text data.

As described above, the text data converted from the speech information is transmitted from a text data transmission/reception unit 107 to a text data storage unit 108 and stored therein. The text data stored in the text data storage unit 108 is displayed on the monitor 3 of the terminal device 2 through a display device 30 that will be described later.

2. Medical Examination Support Information System Unit

The medical examination support information system unit 20 creates medical examination support information including medical records on the basis of the text data processed by the speech information system unit 10. Hereinafter, a main configuration of the medical examination support information system unit 20 will be described.

[Template Storage Unit]

A template storage unit 201 stores, in advance as a template, instruction content for a large language model 205, which is artificial intelligence for creating medical examination support information. The medical examination support information includes a medical record which serves as an electronic medical chart, a summary briefly summarizing medical examination content to be presented to an owner, and various documents of medical examination details calculated on the basis of the medical examination content (see FIGS. 8 to 10 as an example of the medical examination support information).

Here, as items of the medical record, "chief complaint," "owner's anxiety," "type of disease differentiation/suspected injury and disease names/diagnosis," "orientation of test/test name/test result/treatment content," "treatment policy/treatment plan," "prescription," "next visit," "others (for example, explanation of test result)," and the like are provided.

Furthermore, as items of the summary, for example, items such as "compliance with drug treatment," "meal management," "periodic health check," "monitoring of attack," and "environmental management" are provided.

Furthermore, items such as "product name," "product code," "quantity," and "standard price" are provided as items of the medical examination details.

Here, the medical examination support information is not necessarily limited to the medical record, the summary, and the medical examination details described above. The medical examination support information may include any one of a medical record, a summary, and medical examination details, or a combination of two or more, or a document information regarding medical examination may be added as the medical examination support information as appropriate.

FIGS. 5A and 5B illustrate an example of data content stored in the template storage unit 201. The template storage unit 201 includes a main table and a sub-table, and in the main table, as illustrated in FIG. 5A, the name of a template and a category of the medical examination support information are managed with individual IDs. In addition, as illustrated in FIG. 5B, in the sub-table, specific instruction content (prompt) for input items of the medical examination support information and IDs of parent tables associated with the instruction content are managed with individual IDs.

Regarding the prompt registered in the sub-table, for example, for the input item of "chief complaint" of the medical examination information, specific instruction content for the large language model 205 is registered for each input item, such as "Please summarize the conversation focusing on <owner's chief complaint>. Please describe the purpose of today's examination with the owner's eyes." As other instruction content, for example, templates including various prompts, such as "not using an honorific expression," "only facts obvious from the content of the conversation are answered without presumption," "the name of the pet is recorded, and the name of the person is described as an <owner> or a <veterinarian>," are registered at the time of creating the medical examination support information.

Here, in order to improve the accuracy of the output from the large language model 205, it is preferable to register more specific instruction content as in the template described above, but FIGS. 5A and 5B are examples, and content is not necessarily limited to the content of the template. The content of the template to be registered in the sub-table can be modified by a veterinarian as appropriate according to the type and content of the medical examination support information to be created.

Further, a data structure of the template storage unit 201 does not necessarily need to include a main table and a sub-table. For example, the main table and the sub-table may be integrated and stored as one piece of table data, or may be stored in a data format other than the table data.

[Medical Examination Analysis Unit]

A medical examination analysis unit 202 has a function of specifying a template considered to be appropriate according to the medical examination content of the pet on the basis of the conversation content converted into text data and calling the specified template from the template storage unit 201.

Note that it is not always necessary to call a template from the template storage unit 201 via the medical examination analysis unit 202, and for example, any template selected by a veterinarian may be called.

[Medical Examination Information Acquisition Unit]

A medical examination information acquisition unit 203 acquires various types of data including text data created by the speech information system unit 10, a template called by the medical examination analysis unit 202, and past medical chart information stored in a medical examination support information storage unit 209 that will be described later in a case where a pet that is a medical examination target is to be re-examined. The acquired data is organized as input parameters for the large language model 205.

Here, as the medical chart information, various types of information such as basic information of a pet (a name, a weight, a body temperature, and the like), a previous medical examination date, and previous diagnosis content and treatment content are acquired and reflected in medical examination support information created at the time of current medical examination. Note that, in a case where a pet that is a medical examination target is a new patient and there is no past medical history, the basic information of the pet may be entered by predetermined input means such as manual entry by a veterinarian.

In addition, the medical examination information acquisition unit 203 is not necessarily provided, and input parameters including various types of data may be configured to be directly input to a medical examination support information creation unit 204 that will be described later, organized as input parameters, and output to the large language model 205.

[Medical Examination Support Information Creation Unit]

The medical examination support information creation unit 204 creates medical examination support information on the basis of the large language model 205 which is artificial intelligence by using the various types of data acquired by the medical examination information acquisition unit 203 as input parameters. The large language model 205 is a language model trained with a large amount of data such as articles, books, and websites on the Internet. The large language model 205 has a function of, when the above template is filled, analyzing the text data generated by the speech information system unit 10 and automatically generating input information to each input item of the medical examination support information.

[Artificial Intelligence Control Unit]

An artificial intelligence control unit 206 has a function of making a process of sending a request to the large language model 205 into a task and managing the task until the completion of the process so that the transmitted request is appropriately processed. The artificial intelligence control unit 206 serves the role of, for example, providing a notification of a predicted time required to create the medical examination support information, managing the processing order of a plurality of requests, or managing a coping method in a case of an error occurred in information during the generation of input information, so that the quality of the generation process in the large language model is maintained.

[Fee Storage Unit]

As illustrated in FIG. 6, in a fee storage unit 207, fees for medical examination items are registered in association with each other. The medical examination items registered in the fee storage unit 207 can be added or deleted by a veterinarian as appropriate, and fees for the medical examination items can also be modified as appropriate according to the fee revision.

[Medical Examination Details Analysis Unit]

A medical examination details analysis unit 208 has a function of extracting a medical examination item included in the text data as a result of analysis by the large language model 205, referring to the fee information stored in the fee storage unit 207 for the extracted medical examination item, and calculating a medical examination fee to create medical examination details.

Specifically, when words related to medical examination items such as a "blood test," "abdomen echo," and a "urine test" in the text data are detected, the medical examination details analysis unit 208 refers to the fees corresponding to these words from the fee storage unit 207. On the basis of the reference results, medical examination details as accounting information of the current medical examination are created.

In addition, as described above, the medical examination details analysis unit 208 is not limited to the case of extracting only an item in which a word in the text data and a word stored in the fee storage unit 207 exactly match each other as medical examination details, and may extract a medical examination item including a partially matching word. For example, in a case where the word "test of blood" is detected in the text data, "blood test" and "blood biochemical test" may also be extracted as candidates for the medical examination item as a test item related to "blood." Note that, when medical examination items are extracted including partially matching words, unnecessary medical examination items may also be reflected in the medical examination details. In this case, a veterinarian can appropriately delete the unnecessary medical examination items.

As described above, the medical examination support information created by the large language model 205 is stored in the medical examination support information storage unit 209. The medical examination support information storage unit 209 includes a medical record storage unit 209a, a summary storage unit 209b, and a medical examination details storage unit 209c, and the medical examination support information is stored in each storage unit.

3. Display Device

The display device 30 has a function of displaying the medical examination support information created by the medical examination support information system unit 20 on the monitor 3 of the terminal device 2 on the basis of an input signal from the medical examination support information system unit 20.

Figure 7:
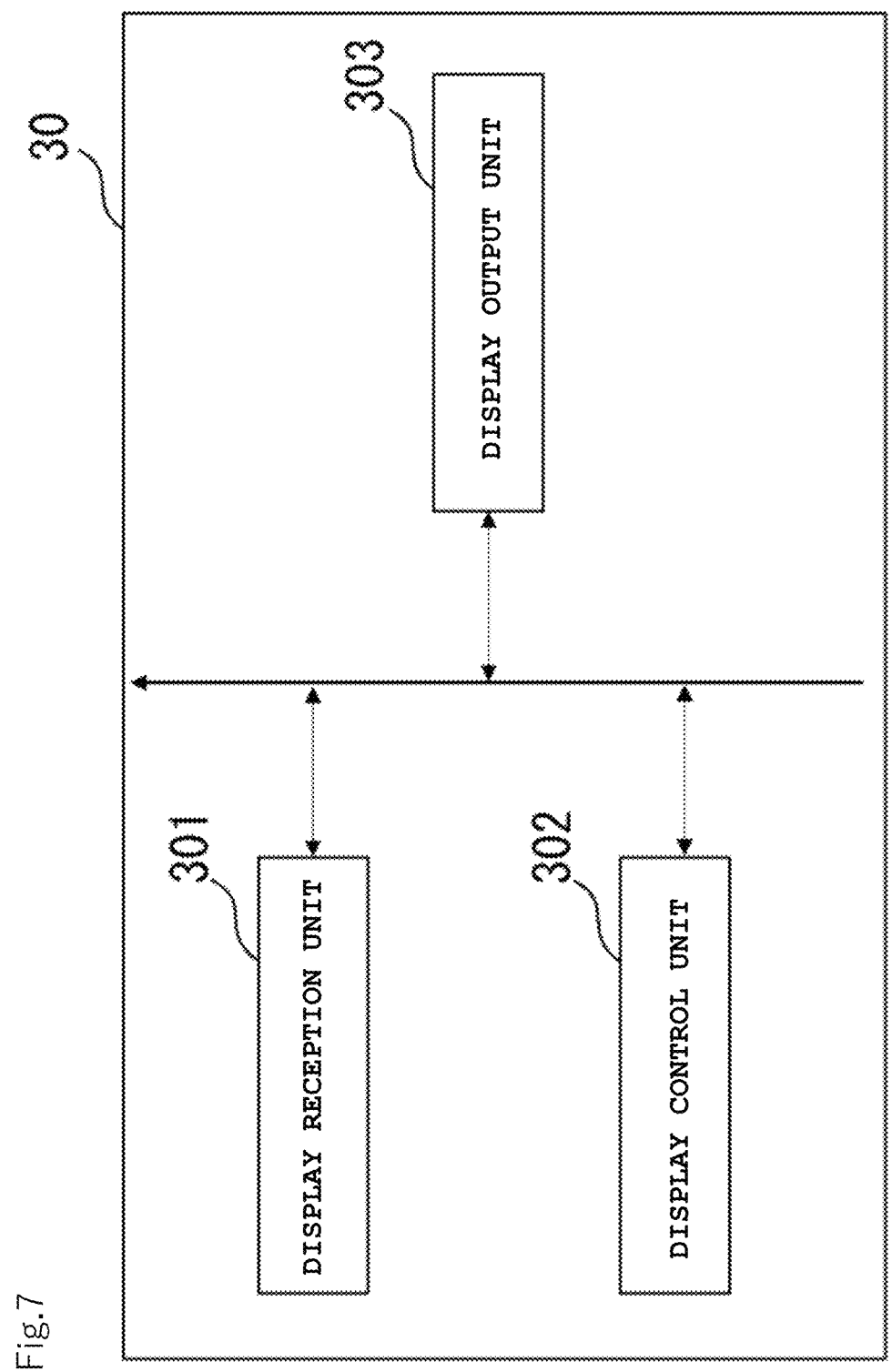
FIG. 7 is a block diagram illustrating an internal configuration of a display device.

FIG. 7 illustrates a block diagram of the display device 30. When a display reception unit 301 receives an operation signal from a veterinarian, a display control unit 302 selects display content to be displayed on the monitor 3 and transmits the display content to a display output unit 303. The display content is displayed on the monitor 3 on the basis of an output signal from the display output unit 303.

Figure 10:
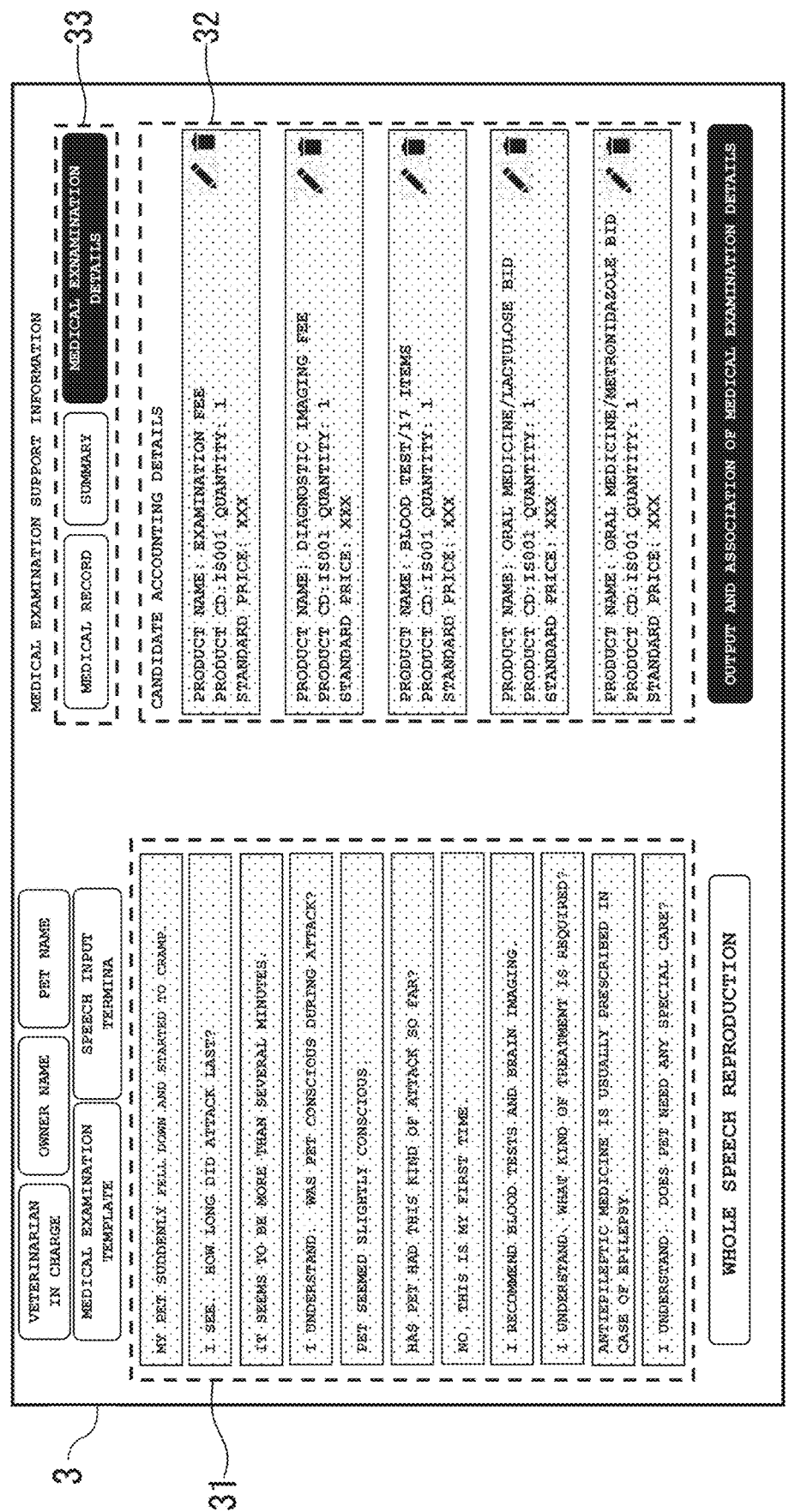
FIG. 10 is a diagram illustrating an example of a display screen in a state in which medical examination details of the medical examination support information are displayed on the monitor.

FIGS. 8 to 10 are diagrams illustrating an example of a display screen in a state in which the medical examination support information is displayed on the monitor 3. The monitor 3 has two large display units such as a first display unit 31 and a second display unit 32, and basic information such as a veterinarian name, an owner name, and a pet name is displayed around the two display units, and operation buttons for performing predetermined operations are laid out.

First, text data indicating the conversation content created by the speech information system unit 10 is displayed on the first display unit 31. In this case, the text data indicating the conversation content displayed on the first display unit 31 is displayed in chronological order by dividing the text data into phrases of the conversation for each speaker specified by the speech input control unit 104.

When the text data of each piece of conversation content displayed on the first display unit 31 is pressed with, for example, a mouse or a finger on a screen, speech information of each pressed conversation content is reproduced. In addition, when the "whole speech reproduction" button below the first display unit 31 is similarly pressed with the mouse or the finger on the screen, speech information of the whole conversation is reproduced. Therefore, the veterinarian can check the content of the text data together with the speech information.

Next, the medical examination support information created by the medical examination support information system unit 20 is displayed on the second display unit 32. A selection unit 33 that selects medical record information to be displayed on the second display unit 32 is provided above the second display unit 32. When a veterinarian performs input with each selection button of "medical record," "summary," and "medical examination details" displayed on the selection unit 33, an input signal thereof is received by the display reception unit 301, and the selected medical record information is called from the medical examination support information storage unit 209 and output from the display output unit 303 to the monitor 3.

Here, FIG. 8 illustrates a screen for which "medical record" is selected in the selection unit 33, FIG. 9 illustrates a screen for which "summary" is selected in the selection unit 33, and FIG. 10 illustrates a screen for which "medical examination details" is selected in the selection unit 33.

In the medical examination support information, the medical record is used as an electronic medical chart to be confirmed by a medical worker including a veterinarian, and the summary is printed out as necessary and provided to an owner at the end of medical examination. In addition, the medical examination details are used at the time of accounting at the end of medical examination in cooperation with an accounting system of a hospital.

In a case where the veterinarian checks the text data of the medical examination support information displayed on the monitor 3 and determines that correction of erroneous conversion or correction of expression is further necessary, the veterinarian corrects the text data as appropriate on the basis of the administrator authority of the terminal device 2, and the corrected medical examination support information is stored in the medical examination support information storage unit 209 as an overwriting of the original data or as a separate file.

Figure 11:
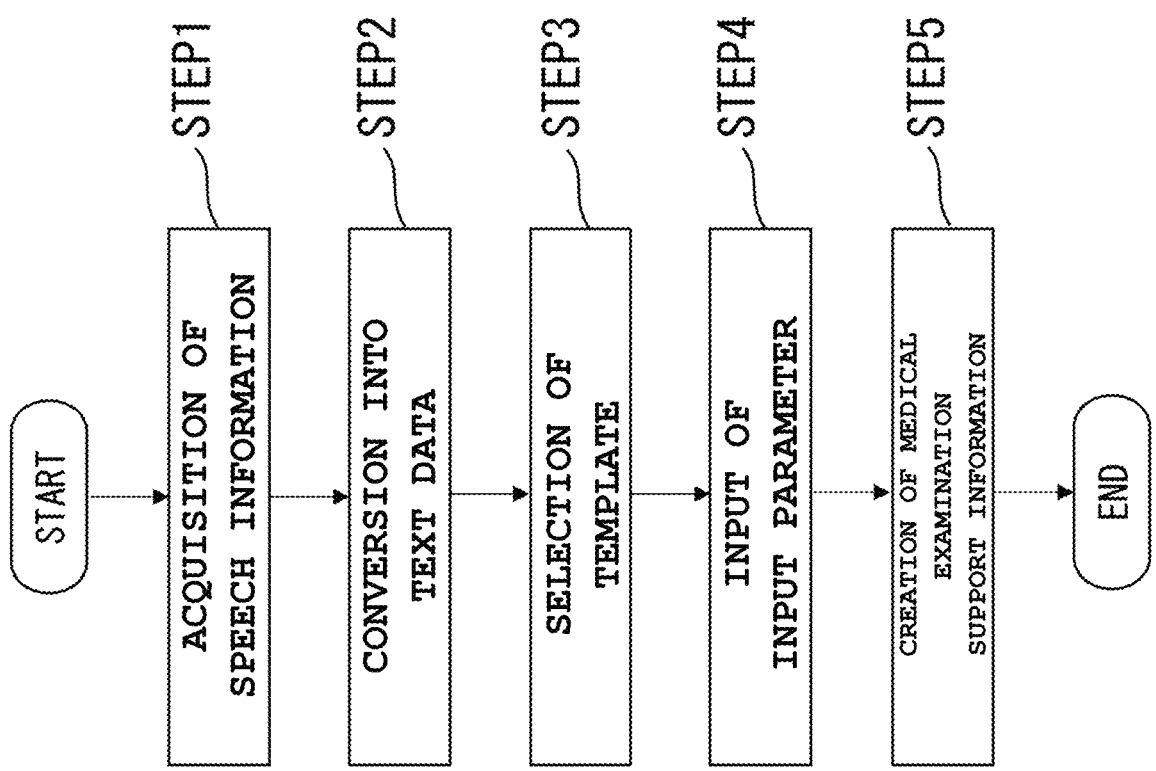
FIG. 11 is a diagram illustrating a calculation flow of a medical examination support program according to an embodiment of the present invention.

The configurations of the medical examination support system 1 and the display device 30 according to the embodiment of the present invention have been described above. Next, a medical examination support program executed by the medical examination support system 1 will be described with reference to a flowchart of FIG. 11.

First, the speech input unit 101 acquires speech information of conversation between a veterinarian and an owner under medical examination, and the acquired speech information is stored in the speech information storage unit 103 (STEP 1).

Next, the speech information stored in the speech information storage unit 103 is converted into text data by the text data conversion unit 106 (STEP 2).

Next, a template of instruction content to be created for the large language model 205 is selected from the templates stored in the template storage unit 201 (STEP 3).

Next, the text data and the template are input as input parameters to the large language model 205 of the medical examination support information creation unit 204 (STEP 4).

On the basis of the input values in STEP4, medical examination support information is created from the text data on the basis of the large language model 205 (STEP 5).

By repeating the calculations in STEPS 1 to 5, it is possible to automatically create the medical examination support information on the basis of the speech information of the conversation between the veterinarian and the owner.

The medical examination support system, the display device, and the medical examination support program according to the embodiment of the present invention have been described above. In the above description, the embodiment in which the medical examination support information is created on the basis of conversation between a veterinarian and a pet owner in an animal hospital has been described, but the present invention can also be applied to other embodiments. For example, in a case where the present invention is applied to human medical care, it is possible to create medical examination support information on the basis of conversation between a doctor and a patient.

As described above, the medical examination support system, the display device, and the medical examination support program according to the present invention can create a medical record with high quality on the basis of information of conversation between a veterinarian and an owner in animal medical care, and improve the efficiency of animal medical care.

DESCRIPTION OF REFERENCE SIGNS

1 Medical examination support system
10 Speech information system unit
101 Speech input unit
102 Speech information transmission/reception unit
103 Speech information storage unit
104 Speech input control unit
105 Anti-tampering unit
106 Text data conversion unit
107 Text data transmission/reception unit
108 Text data storage unit
20 Medical examination support information system unit
201 Template storage unit
202 Medical examination analysis unit
203 Medical examination information acquisition unit
204 Medical examination support information creation unit
205 Large language model
206 Artificial intelligence control unit
207 Fee storage unit
208 Medical examination details analysis unit
209 Medical examination support information storage unit
30 Display device
301 Display reception unit
302 Display control unit
303 Display output unit
2 Terminal device
3 Monitor
4 Internet line

What is claimed is:

1. A medical examination support system comprising:
a speech information storage unit that stores speech information of conversation exchanged between a medical worker and a target person having a subject that is a medical examination target;
a text data conversion unit that converts the speech information into text data;
a template storage unit that stores a predetermined template including instruction content for a large language model for creating medical examination support information including at least one of a medical record for the medical worker, a summary for the target person corresponding to the medical record, and medical examination details based on medical examination content; and
a medical examination support information creation unit that creates the medical examination support information on the basis of the large language model with the text data and the template as input parameters, wherein
the text data conversion unit includes:
a dictionary storage unit that stores a medicine name or a medical term including a predetermined single sound for which speech recognition is determined to be difficult;
a word/phrase extraction unit that extracts a predetermined word/phrase including the single sound from text data obtained from the speech information;
a word/phrase determination unit that determines whether or not the word/phrase is a medicine name or a medical term from a context of one sentence including the word/phrase extracted by the word/phrase extraction unit, and, in a case where the word/phrase is determined to be a medicine name or a medical term, determines whether or not the word/phrase is a medicine name or a medical term including a predetermined single sound stored in the dictionary storage unit; and
a word/phrase conversion unit that, in a case where the word/phrase determination unit determines that the word/phrase is not a medicine name or a medical term stored in the dictionary storage unit, converts the word/phrase into a predetermined medicine name or medical term including the single sound stored in the dictionary storage unit.

2. The medical examination support system according to claim 1, wherein
at least one or more input items of a chief complaint, diagnosis content, a treatment plan, treatment content, a prescription, and an explanation of a test result are included as input items of the medical record of the medical examination support information, and
the medical examination support information creation unit creates input information to each input item of the medical record on the basis of the large language model.

3. The medical examination support system according to claim 1, wherein
at least one or more input items of a method of administering a prescription drug to the subject, meal management of the subject, monitoring of a condition of the subject, management of a living environment of the subject, and a next scheduled medical examination date of the subject are included as input items of the summary of the medical examination support information, and
the medical examination support information creation unit creates input information to each input item of the summary on the basis of the large language model.

4. The medical examination support system according to claim 1, further comprising:
a fee storage unit that is associated with a medical fee corresponding to a medical examination item, wherein
the medical examination support information creation unit calls a medical fee corresponding to a medical examination item extracted on the basis of the large language model from the fee storage unit, and creates input information to an input item of the medical examination details.

5. The medical examination support system according to claim 1, further comprising:
   a medical examination support information storage unit that stores the medical examination support information created by the medical examination support information creation unit, wherein
   at the time of the next medical examination of the subject, basic information of the subject is acquired from the medical examination support information stored in the medical examination support information storage unit.

6. The medical examination support system according to claim 1, wherein
   the speech information stored in the speech information storage unit is subjected to a predetermined anti-tampering process.

7. A non-transitory computer-readable medium storing a computer program for causing a computer to execute:
   a step of acquiring speech information of conversation exchanged between a medical worker and a target person having a subject that is a medical examination target;
   a step of converting the speech information into text data;
   a step of selecting a template including instruction content for a large language model for creating medical examination support information including at least one of a medical record for the medical worker, a summary for the target person corresponding to the medical record, and medical examination details based on medical examination content;
   a step of inputting the text data and the template to the large language model as input parameters; and
   a step of creating the medical examination support information from the text data on the basis of the large language model to which the input parameters have been input, wherein
   the step of converting the speech information into text data includes:
   a step of extracting a word/phrase including a predetermined single sound for which speech recognition is determined to be difficult from text data obtained from the speech information,
   a step of determining whether the word/phrase is a medicine name or a medical term from a context of one sentence including the extracted word/phrase,
   a step of, in a case where the word/phrase is determined to be a medicine name or a medical term, determining whether or not the word/phrase is a medicine name or a medical term including a predetermined single sound stored in advance, and
   a step of, in a case where it is determined that the word/phrase is not a medicine name or a medical term including the predetermined single sound stored in advance, converting the word/phrase into a medicine name or medical term including the predetermined single sound stored in advance.

8. A medical examination support system comprising a processor and a memory,
   wherein the memory is configured to:
   store speech information of conversation exchanged between a medical worker and a target person having a subject that is a medical examination target;
   store a medicine name or a medical term including a predetermined single sound for which speech recognition is determined to be difficult
   store a predetermined template including instruction content for a large language model for creating medical examination support information including at least one of a medical record for the medical worker, a summary for the target person corresponding to the medical record, and medical examination details based on medical examination content;
   and wherein the processor is configured to:
   convert the speech information into text data;
   create the medical examination support information on the basis of the large language model with the text data and the template as input parameters,
   extract a predetermined word/phrase including the single sound from text data obtained from the speech information;
   determine whether or not the word/phrase is a medicine name or a medical term from a context of one sentence including the word/phrase extracted by the processor and in a case where the word/phrase is determined to be a medicine name or a medical term, determine whether or not the word/phrase is a medicine name or a medical term including the predetermined single sound stored in the memory;
   and in a case where the processor determines that the word/phrase is not a medicine name or a medical term stored in the memory, convert the word/phrase into a predetermined medicine name or medical term including the single sound stored in the memory.

* * * * *